(12) United States Patent
Watanabe et al.

(10) Patent No.: US 8,440,659 B2
(45) Date of Patent: May 14, 2013

(54) TERMITE-PROOFING AGENT AND ITS APPLICATION METHOD

(75) Inventors: Kunitoshi Watanabe, Saitama (JP); Toshio Suzuki, Kumamoto (JP); Suguru Shinya, Kumamoto (JP)

(73) Assignee: LANXESS Deutschland GmbH, Leverkusen (DE)

( * ) Notice: Subject to any disclaimer, the term of this patent is extended or adjusted under 35 U.S.C. 154(b) by 1276 days.

(21) Appl. No.: 10/598,615

(22) PCT Filed: Mar. 10, 2005

(86) PCT No.: PCT/JP2005/004717
§ 371 (c)(1),
(2), (4) Date: Jul. 2, 2007

(87) PCT Pub. No.: WO2005/084442
PCT Pub. Date: Sep. 15, 2005

(65) Prior Publication Data
US 2008/0015168 A1    Jan. 17, 2008

(30) Foreign Application Priority Data
Mar. 10, 2004 (JP) ................. 2004-066675

(51) Int. Cl.
| A01N 43/90 | (2006.01) |
| A01N 43/40 | (2006.01) |
| A01N 43/08 | (2006.01) |
| A01N 43/78 | (2006.01) |
| A01N 47/40 | (2006.01) |
| A01N 51/00 | (2006.01) |
| B27K 3/02  | (2006.01) |
| B27K 5/00  | (2006.01) |

(52) U.S. Cl.
USPC ........ 514/229.2; 514/357; 514/365; 514/471

(58) Field of Classification Search ............... 514/229.2, 514/341, 357, 365, 471
See application file for complete search history.

(56) References Cited

U.S. PATENT DOCUMENTS
6,376,487 B1    4/2002  Maienfisch et al.
2003/0181448 A1 *  9/2003  Senn .................... 514/229.2

FOREIGN PATENT DOCUMENTS
| EP | 0580553 A2 | 7/1993 |
| EP | 1293122 A1 | 3/2003 |
| WO | 02/17220 A1 | 3/2002 |
| WO | 02/052940 A1 | 7/2002 |
| WO | WO 2004/108372 | * 12/2004 |

OTHER PUBLICATIONS
Machine translation of JP 08-175914 (1996).*
Human translation (partial) of JP 08-175914 (1996).*
The Southern Pines publication, U.S. Department of Agriculture, U.S. Forest Service, Publication FS-256, pp. 1-10 (Jul. 1985).*
Kim Chul-Su et al: "Chemical control of sycamore lace bug, Corythucha ciliata(Say)"; Journal of Korean Forestry Society; vol. 89, No. 3 (Sep. 2000).
Grosman Donald M et al: "Systemic and seed insects in loblolly pine seed orchards: 2 year results"; Southern Journal of Applied Forestry; vol. 26, No. 3 (Aug. 2002).
Derwent: "Solubilised formulation for injecting into wood trunk to inhibit withering of pine trees—contains e.g. insecticide, solubilising agent contg nonionic surfactant and solvent" (1996).

* cited by examiner

*Primary Examiner* — John Pak
(74) *Attorney, Agent, or Firm* — Nicanor A. Kohncke

(57) ABSTRACT

The present invention is a composition comprising a neonicotinoid-based compound having a high degree of insecticide activity, an organic solvent and a surfactant. The present invention is also a method that allows the obtaining of lumber that does not require termite-proofing treatment following production of lumber by injecting this composition into a tree trunk and allowing the chemical to circulate and disperse within the tree trunk.

7 Claims, No Drawings

TERMITE-PROOFING AGENT AND ITS APPLICATION METHOD

This application is a 371 of International Application No. PCT/JP2005/004717 filed Mar. 10, 2005, which claims priority to JP 2004-066675 filed Mar. 10, 2004, the contents of which are incorporated herein by reference.

TECHNICAL FIELD

The present invention is a tree trunk injection preparation and a method for producing lumber that does not require termite-proofing treatment following lumber production by applying the tree trunk injection preparation.

More than twenty species of termites such as Japanese termites and Oriental termites thrive in Japan, and their resulting damage to wooden structures is so extensive that it is referred to as "flame-less fire". Since lumber is used in the traditional Japanese construction method of wooden framework construction and the conventional construction method employed in North America of framed wall construction in particular, once such structures become damaged by termites, the resulting damage can be to the extent to which the structure must be rebuilt. Even in the case of using a steel frame or reinforced concrete for the structural materials, since wood is frequently used for the inner walls and interior, there are many reports of termite damage in these cases as well.

In the Kyushu, Shikoku, Chugoku, Kansai and Tokai regions where Oriental termites thrive, the dissemination of insecticide into the soil and the spraying of insecticide onto wooden structural sections one meter or less above ground are essential for preventing termites during the construction of wooden structures. In addition, preventive treatment for soil under the floors and wooden sections must be repeated by spraying with chemicals every three to five years.

Termite damage frequently occurs at locations out of view, such as within structural materials, beneath floors and inside walls, and the work involved to exterminate termites in these locations is frequently difficult.

Although various methods of chemical treatment are employed for the wood used in order to protect a structure from termite damage, each of these treatment methods has its own advantages and disadvantages, such as the work efficiency of chemical treatment, limitations due to the physical properties of the chemicals, and problems with toxicity for the workers and the environment.

BACKGROUND ART

Examples of methods that have been employed in the prior art for rot-proofing and termite-proofing structural wooden materials include (1) injection into the trunks of standing trees, (2) chemical treatment of the cut ends of felled timber, (3) coating and spraying lumber with chemicals, (4) immersing lumber in chemicals, and (5) injecting chemicals into lumber under pressure.

The method involving injection into the trunks of standing trees is an easy method, but it has poor treatment efficiency since considerable time is required to inject a large amount of chemical in treating individual trees, and the chemical used must be soluble in water. Thus, this method is hardly used at all at present.

Height difference injection methods are typically used for treating the cut ends of felled timber with chemicals. Examples of such methods include the Bushley method, in which the cross-sectional surfaces of the bases of bark-covered logs are coupled with a chemical tank installed at a high location immediately after felling followed by the injection of chemical utilizing the water pressure resulting from this height difference, and a method in which, after peeling the bark for a distance of about 10 cm from the base of bark-covered logs, the peeled base is covered with one end of a tire tube and fastened to the log with wire or a rubber band, after which chemical is injected into the tube from the other end and the base of the log is inclined at a steep angle and allowed to stand undisturbed. These methods are also hardly used for the same reasons as the aforementioned method involving injection into the trunks of standing trees.

Methods involving coating or spraying lumber with chemicals are the most common methods of rot-proofing and termite-proofing treatment, and are routinely employed at building construction sites. In these methods, an emulsion or wettable powder containing rot-proofing and termite-proofing ingredients is diluted with water, a chemical in which the termite-proofing ingredient is diluted with kerosene is applied to the lumber with a brush, or the chemical is sprayed onto the lumber with a sprayer. However, these methods have the shortcomings of requiring considerable time and trouble for treatment, the surfaces to which the chemical adheres are extremely limited to unevenness of coating or spraying, and the chemical being unable to be adequately impregnated into the lumber, thereby making lumber susceptible to infiltration by putrefying microorganisms and termite from those sections where the chemical has not adhered or only adhered in a small amount. In addition, there is also the problem of environmental contamination since the chemical sprays onto lumber other than the lumber targeted for spraying.

Although the method involving immersing lumber in a chemical allows the chemical to be more reliably impregnated into the lumber than the aforementioned coating or spraying, it has the shortcomings of requiring the providing of a large immersion tank and a large volume of chemical so that the lumber to be treated can be completely immersed.

Although methods involving the injection of a chemical into lumber under pressure enable chemicals to reliably penetrate inside the lumber in a short period of time, they also have the shortcomings of requiring a device to generate pressure, requiring a large amount of chemical in the same manner as immersion methods, and require measures for preventing pollution with respect to treating the waste chemical following treatment. Although CCA (chromium-copper-arsenic) compounds having both termite-proofing and rot-proofing effects have been used as chemicals in these methods, treatment using this method is decreasing rapidly for the reasons mentioned above.

As has been previously described, although there are numerous methods for termite-proofing treatment of lumber, since each of these methods have problems, treatment is performed by selecting the method thought to be optimum based on the respective situation. Among these, although injection into the trunks of standing trees provides a simple method that is easy to implement, since it requires the injection of a large amount of chemical and considerable time is required for that injection, it is currently hardly employed at all for reasons of poor treatment efficiency. However, it is thought that this method would proliferate considerably if an active ingredient or preparation were available that would enable treatment to be performed with a small amount of chemical and in a short period of time.

DISCLOSURE OF INVENTION

Neonicotinoid-based compounds are compounds that have a high degree of termite insecticide action, have low toxicity with respect to people and exhibit very little dissipation in air, and several of these compounds are used practically as termite control chemicals. However, since neonicotinoid-based compounds are essentially insoluble in water or only a very small amount dissolves in water, they are nearly always used in the form of a wettable powder. Lumber treated with a termite-proofing agent can be obtained as a result of allowing easy injection into tree trunks and circulating within the tree body by combining a neonicotinoid-based insecticide component with a solvent miscible in water and a surfactant.

BASE MODE FOR CARRYING OUT THE INVENTION

The present invention relates to a tree trunk injection preparation comprising (1) a neonicotinoid-based insecticide component that is virtually insoluble in water or only a very small amount of which dissolves in water, (2) a solvent miscible in water, and (3) a surfactant, and to a method for obtaining lumber that does not require termite-proofing treatment following lumber production by injecting said tree trunk injection preparation into the trunk of a tree such as pine, cedar or cypress and circulating inside the tree body.

Although compounds such as nitenpyram, imidacloprid and thiacloprid are also effective as neonicotinoid-based insecticide components in addition to those indicated in claim 1, organic phosphorus-based insecticides such as acephate, fenitrothion, ethylthiometon and diazinon, synthetic pyrethroid-based insecticides such as permethrin, etofenprox and silafluofen, and carbamate-based insecticides such as oxamyl, methomyl and benfuracarb are also effective.

In addition, disinfectants for rot-proofing may also be used alone or mixed with the aforementioned insecticides.

The solvent used in the composition of the present invention is preferably that which is easily miscible with water, examples of which include lower alcohols such as methanol and ethanol, ethers such as dioxane and tetrahydrofuran, ketones such as methyl ethyl ketone and cyclohexanone, esters such as ethyl acetate and butyl acetate, sulfoxides such as dimethylsulfoxide, nitriles such as acetonitrile, pyrrolidones such as N-methylpyrrolidone and N-ethylpyrrolidone, amides such as N,N-dimethylformamide, and glycols such as ethylene glycol, propylene glycol and diethylene glycol, their esters and their ethers.

Examples of surfactants used in the composition of the present invention include anionic surfactants such as alkyl sulfate esters, alkane sulfonates, alkyl benzene sulfonates, alkyl phosphate esters, N-acyl sarcosine salts, N-acyl alanine salts and succinates, cationic surfactants such as alkyl amines, alkyl trimethyl ammonium salts, dialkyl dimethyl ammonium salts, alkyl dimethyl benzyl ammonium salts and alkyl pyridinium salts, and nonionic surfactants such as polyoxyethylene castor oils, polyoxyethylene hardened castor oils, polyoxyethylene alkyl ethers, polyoxyethylene alkyl phenyl ethers, polyoxyethylene alkyl phenyl ether formaldehyde condensation products, polyoxyethylene allyl phenyl ethers, polyoxyethylene allyl phenyl ether formaldehyde condensation products, polyoxyethylene glycol fatty acid esters, polyoxyalkylene alkyl ethers, sorbitan fatty acid esters, polyoxyethylene sorbitan fatty acid esters, polyoxyethylene sorbitol fatty acid esters, polyglycerin fatty acid esters, sucrose fatty acid esters and propylene glycol mono fatty acid esters.

Among these, a suitable nonionic surfactant is normally used alone or as a mixture with anionic surfactant. Preferable examples of nonionic surfactants include polyoxyethylene hardened castor oils, polyoxyethylene alkyl ethers, polyoxyalkylene alkyl ethers, polyoxyethylene allyl phenyl ethers and polyoxyethylene sorbitan fatty acid esters.

Since the composition cannot be injected into a tree body if its viscosity is excessively high, normally it is preferable to use solvent and surfactant having low viscosity.

Although the amount of each component of the composition of the present invention can be suitably changed, active ingredient can be contained at about 0.1 to 20% by weight and preferably about 1 to 10% by weight, solvent can be contained at about 30 to 90% by weight and preferably about 40 to 70% by weight, and surfactant can be contained at about 0 to 20% by weight and preferably about 0 to 10% by weight.

The composition of the present invention is prepared by uniformly dissolving each component. The preparation method involves mixing and dissolving the total amount of components using a stirrer in a suitably large tank.

The method for applying the present composition to trees consists of drilling a hole in the trunk with a drill and so forth at a location lower than the site where the tree is felled, and injecting the composition of the present invention contained in a suitable container either without applying pressure or under pressure. Although the amount applied varies according to the content of active ingredient and the timber volume of the tree, in the case of a preparation having an active ingredient content of 3 to 5%, the applied amount is 100 to 1000 ml, and preferably 200 to 600 ml, per cubic meter of timber volume. In addition, it is preferable to inject the preparation into the tree trunk using at least two locations, and preferably 2 to 5 locations, so that the preparation is uniformly dispersed within the tree trunk.

A further embodiment of the present invention is a method for obtaining a lumber product, comprising the steps of:

preparing a liquid mixture;

injecting said liquid mixture into a living tree;

thereafter felling said living tree and allowing it to air dry for three months; and subsequently, processing said felled tree into said lumber product;

wherein said liquid mixture comprises a neonicotinoid-based insecticide component selected from the group consisting of thiamethoxam, acetamiprid, dinotefuran and clothianidin, said neonicotinoid-based insecticide component being virtually insoluble in water or only a very small of which dissolves in water, at least one solvent miscible in water, and at least one surfactant, and further wherein the processing of said felled tree into said lumber product does not include a termite-proofing treatment.

EXAMPLES

The following provides a detailed explanation of the contents of the present invention through examples, but the present invention is not limited to these examples.

Example 1

Formulation of Injection Preparation

Formulation examples of an injection preparation having a neonicotinoid-based compound in the form of thiamethoxam as their active ingredient are shown in Table 1.

TABLE 1

Injection Preparation Formulations

| | Formula No. | | | | | | | | | |
|---|---|---|---|---|---|---|---|---|---|---|
| | 1 | 2 | 3 | 4 | 5 | 6 | 7 | 8 | 9 | 10 |
| Thiamethoxam bulk drug | 4.0 | 4.0 | 4.0 | 4.0 | 4.0 | 4.0 | 4.0 | 4.0 | 4.0 | 4.0 |
| Cyclohexanol | | | | | | | | | | 30.0 |
| Diethylene glycol | 30.0 | | | | | | | | | |
| Cyclohexanone | | 30.0 | | | 20.0 | 20.0 | 20.0 | 20.0 | 20.0 | |
| N-methylpyrrolidone | | | 30.0 | | | | | | | |
| N,N-dimethylformamide | | | | 30.0 | | | | | | |
| Acetone | 20.0 | 20.0 | 20.0 | 20.0 | 20.0 | 20.0 | 20.0 | 20.0 | 20.0 | 20.0 |
| Methanol | 31.0 | 31.0 | 31.0 | 31.0 | 41.0 | 41.0 | 41.0 | 41.0 | 41.0 | 31.0 |
| Water | 5.0 | 5.0 | 5.0 | 5.0 | 5.0 | 5.0 | 5.0 | 5.0 | 5.0 | 5.0 |
| NK100[1]) | 10.0 | 10.0 | 10.0 | 10.0 | | | | | | |
| NK135[2]) | | | | | 10.0 | | | 7.0 | 7.0 | 10.0 |
| NK1372[3]) | | | | | | 10.0 | | | | |
| NK1548[4]) | | | | | | | 10.0 | | | |
| NK41C[5]) | | | | | | | | 3.0 | | |
| NK41B[6]) | | | | | | | | | 3.0 | |
| Total | 100.0 | 100.0 | 100.0 | 100.0 | 100.0 | 100.0 | 100.0 | 100.0 | 100.0 | 100.0 |

Notes:
1)Polyoxyethylene hardened castor oil
2)Polyoxyethylene styryl phenyl ether
3)Polyoxyethylene nonyl phenyl ether
4)Polyoxyethylene oleyl ether
5)Calcium alkyl benzene sulfonate
6)Sodium alkyl benzene sulfonate Although any of the preparations shown in Table 1 can be used, those which do not cloud or precipitate when diluted in water, and have a preparation viscosity (Type B viscometer) that allows them to be injected rapidly are preferable.

Example 2
Injection into Tree

The preparation of Formula No. 9 among the formulas shown in Example 1 was injected into the trunks of 20-40 year old pine trees at a location 30 cm above the ground at 200, 400 and 600 ml per cubic meter of timber volume. Injections were made without applying pressure and under pressure, and the preparation was injected into three trees for each injection volume.

In addition, the preparation was injected into trunks of about 30 year old cedar trees in the same manner as the pine trees.

TABLE 2

Injection of Preparation into Standing Pine Trees

| Trunk Injection per cubic meter | Trunk diameter of tree at the height of chest (cm) | Height of tree (m) | Timber volume (m3) | Injection volume (ml) | Number of hole(s) on injection container | Injection method | Time for injection (min) |
|---|---|---|---|---|---|---|---|
| 200 ml | 18 | 12 | 0.16 | 32 | 1 | Without applying pressure | 45 |
| | 22 | 14 | 0.26 | 52 | 2 | Without applying pressure | 30 |
| | 25 | 18 | 0.4 | 80 | 2 | Without applying pressure | 45 |
| | 20 | 12 | 0.19 | 38 | 1 | Under pressure | 15 |
| | 25 | 15 | 0.3 | 60 | 2 | Under pressure | 12 |
| | 25 | 18 | 0.4 | 80 | 2 | Under pressure | 20 |
| 400 ml | 20 | 13 | 0.2 | 80 | 2 | Without applying pressure | 55 |

TABLE 2-continued

Injection of Preparation into Standing Pine Trees

| Trunk Injection per cubic meter | Trunk diameter of tree at the height of chest (cm) | Height of tree (m) | Timber volume (m3) | Injection volume (ml) | Number of hole(s) on injection container | Injection method | Time for injection (min) |
|---|---|---|---|---|---|---|---|
| | 22 | 16 | 0.29 | 116 | 2 | Without applying pressure | 70 |
| | 28 | 20 | 0.54 | 216 | 3 | Without applying pressure | 70 |
| | 18 | 13 | 0.17 | 68 | 2 | Under pressure | 15 |
| | 20 | 15 | 0.23 | 92 | 2 | Under pressure | 25 |
| | 24 | 18 | 0.39 | 156 | 3 | Under pressure | 40 |
| 600 ml | 20 | 12 | 0.19 | 114 | 2 | Without applying pressure | 70 |
| | 25 | 15 | 0.3 | 180 | 3 | Without applying pressure | 60 |
| | 29 | 20 | 0.58 | 348 | 5 | Without applying pressure | 90 |
| | 19 | 11 | 0.16 | 96 | 2 | Under pressure | 25 |
| | 23 | 13 | 0.26 | 156 | 3 | Under pressure | 25 |
| | 27 | 15 | 0.39 | 234 | 4 | Under pressure | 40 |

Preparations were injected at equal volumes into each hole.
Preparations were pressurized with gas by placing the preparations in a special-purpose pressurizing container.

TABLE 3

Injection of Preparation into Standing Cedar Trees

| Trunk Injection per cubic meter | Trunk diameter of tree at the height of chest (cm) | Height of tree (m) | Timber volume (m$^3$) | Injection volume (ml) | Number of hole(s) on injection container | Injection method | Time for injection (min) |
|---|---|---|---|---|---|---|---|
| 200 ml | 19 | 14 | 0.2 | 40 | 2 | Without applying pressure | 25 |
| | 20 | 15 | 0.23 | 46 | 2 | Without applying pressure | 33 |
| | 20 | 15 | 0.23 | 46 | 2 | Without applying pressure | 35 |
| | 20 | 14 | 0.22 | 44 | 2 | Under pressure | 12 |
| | 20 | 15 | 0.23 | 46 | 2 | Under pressure | 15 |
| | 22 | 15 | 0.28 | 56 | 2 | Under pressure | 18 |
| 400 ml | 20 | 14 | 0.22 | 88 | 2 | Without applying pressure | 50 |
| | 20 | 14 | 0.22 | 88 | 2 | Without applying pressure | 55 |

TABLE 3-continued

Injection of Preparation into Standing Cedar Trees

| Trunk Injection per cubic meter | Trunk diameter of tree at the height of chest (cm) | Height of tree (m) | Timber volume (m³) | Injection volume (ml) | Number of hole(s) on injection container | Injection method | Time for injection (min) |
|---|---|---|---|---|---|---|---|
| | 22 | 15 | 0.28 | 112 | 2 | Without applying pressure | 65 |
| | 20 | 14 | 0.22 | 88 | 2 | Under pressure | 25 |
| | 20 | 14 | 0.22 | 88 | 2 | Under pressure | 25 |
| | 21 | 15 | 0.25 | 100 | 2 | Under pressure | 30 |
| 600 ml | 20 | 14 | 0.22 | 132 | 2 | Without applying pressure | 75 |
| | 20 | 14 | 0.22 | 132 | 2 | Without applying pressure | 80 |
| | 22 | 15 | 0.28 | 168 | 3 | Without applying pressure | 60 |
| | 20 | 14 | 0.22 | 132 | 2 | Under pressure | 35 |
| | 22 | 14 | 0.26 | 156 | 3 | Under pressure | 30 |
| | 22 | 15 | 0.28 | 168 | 3 | Under pressure | 35 |

Preparations were injected at equal volumes into each hole.

Preparations were pressurized with gas by placing the preparations in a special-purpose pressurizing container.

As is shown in Tables 2 and 3, 200 to 600 ml per cubic meter of the preparations were able to be smoothly injected into both the pine trees and cedar trees.

In the case of the pine trees, the preparations were able to be injected in 30 to 90 minutes without applying pressure and in 12 to 40 minutes under pressure. In the case of the cedar trees, the preparations were able to be injected in 25 to 80 minutes without applying pressure and in 12 to 35 minutes under pressure.

Example 3

Termite-Proofing Effects on Wood Treated by Trunk Injection

The pine and cedar trees treated in Example 2 were left standing for 3 months after injection of chemical to allow the chemical to disperse throughout the tree trunk. Three months later, one test tree was appropriately selected from each test area, and cut down at a location 50 cm above the ground. The wood was allowed to air dry for 3 months in the shade, and discs having a thickness of 2 cm were cut starting from the base of the dried wood at 1 m intervals to a length of 4 m followed by obtaining wood blocks measuring 2 cm×2 cm×2 cm from these discs. Sterilized and disinfected sand containing a suitable amount of moisture was placed in the bottom of a glass container having a diameter of 13 cm and height of 3 cm, and the wood blocks were then placed on top of the sand. Ninety worker Oriental termites and 10 soldier Oriental termites were placed in the glass containers containing the wood blocks, and then raised for 4 weeks in a constant temperature thermostat at a temperature of 25 degrees followed by investigating the viability of the termites and the degree of damage to the wood blocks (weight reduction).

Those results are shown in Tables 4 and 5.

TABLE 4

Termite-Proofing Effects on Pine Wood Treated by Trunk Injection

| Trunk Injection per cubic meter | Injection method | Sampling site | | | | | | | |
|---|---|---|---|---|---|---|---|---|---|
| | | 1 m | | 2 m | | 3 m | | 4 m | |
| | | Number of live termites | Weight reduction | Number of live termites | Weight reduction | Number of live termites | Weight reduction | Number of live termites | Weight reduction |
| 200 ml | Without applying pressure | 0 | 0.2 | 0 | 0 | 0 | 0 | 0 | 0 |
| | Under pressure | 0 | 0 | 0 | 0.1 | 0 | 0 | 0 | 0 |

TABLE 4-continued

Termite-Proofing Effects on Pine Wood Treated by Trunk Injection

| Trunk | | Sampling site | | | | | | | |
|---|---|---|---|---|---|---|---|---|---|
| | | 1 m | | 2 m | | 3 m | | 4 m | |
| Injection per cubic meter | Injection method | Number of live termites | Weight reduction | Number of live termites | Weight reduction | Number of live termites | Weight reduction | Number of live termites | Weight reduction |
| 400 ml | Without applying pressure | 0 | 0 | 0 | 0 | 0 | 0 | 0 | 0 |
| | Under pressure | 0 | 0.1 | 0 | 0 | 0 | 0 | 0 | 0 |
| 600 ml | Without applying pressure | 0 | 0 | 0 | 0 | 0 | 0 | 0 | 0 |
| | Under pressure | 0 | 0 | 0 | 0 | 0 | 0 | 0 | 0 |
| Control | | 91 | 224 | 96 | 291 | 92 | 243 | 90 | 240 |

Number of live termites is expressed as the number of termites, while weight reduction is expressed in mg.

The average values are shown obtained by repeating testing three times in each area.

An untreated pine wood block was used as the control.

TABLE 5

Termite-Proofing Effects on Cedar Wood Treated b Trunk Injection

| Trunk | | Sampling site | | | | | | | |
|---|---|---|---|---|---|---|---|---|---|
| | | 1 m | | 2 m | | 3 m | | 4 m | |
| Injection per cubic meter | Injection method | Number of live termites | Weight reduction | Number of live termites | Weight reduction | Number of live termites | Weight reduction | Number of live termites | Weight reduction |
| 200 ml | | 0 | 0 | 0 | 0 | 0 | 0 | 0 | 0 |
| | | 0 | 0.1 | 0 | 0.1 | 0 | 0 | 0 | 0 |
| 400 ml | | 0 | 0 | 0 | 0 | 0 | 0 | 0 | 0 |
| | | 0 | 0 | 0 | 0 | 0 | 0 | 0 | 0 |
| 600 ml | | 0 | 0 | 0 | 0 | 0 | 0 | 0 | 0 |
| | | 0 | 0 | 0 | 0 | 0 | 0 | 0 | 0 |
| Control | | 88 | 176 | 86 | 153 | 91 | 201 | 88 | 177 |

Number of live termites is expressed as the number of termites, while weight reduction is expressed in mg.

The average values are shown obtained by repeating testing three times in each area.

An untreated cedar wood block was used as the control.

As is shown in Tables 4 and 5, none of the Oriental termites survived and there was hardly weight reduction observed in the wood blocks due to termite damage in both pine and cedar wood blocks chemically treated at any of the injection volumes and injection methods.

INDUSTRIAL APPLICABILITY

Instead of treating lumber with a termite-proofing agent by a method such as coating or spraying at the construction site as in the prior art, the present invention allows the obtaining of lumber having a high degree of resistance to termite damage that is not required to be treated with termite-proofing agent at the construction site by injecting a neonicotinoid-based insecticide component into the trunks of standing trees in advance.

As a result of using lumber treated by the present invention, there is no environmental contamination by chemicals since it is not necessary to treat the lumber by coating or spraying a termite-proofing agent at the construction site. In addition, since chemical is dispersed inside the lumber, the effects can be expected to be demonstrated for a long period of time.

The invention claimed is:

1. A method for obtaining a lumber product, comprising the steps of:
   preparing a liquid mixture;
   injecting said liquid mixture into a living tree;
   thereafter felling said living tree and allowing it to air dry for three months; and
   subsequently, processing said felled tree into said lumber product, wherein said liquid mixture comprises
a neonicotinoid-based insecticide component selected from the group consisting of thiamethoxam, acetamiprid, dinotefuran and clothianidin,
said neonicotinoid-based insecticide component being virtually insoluble in water or only a very small amount of which dissolves in water,
at least one solvent miscible in water, and
at least one surfactant, and
further wherein the processing of said felled tree into said lumber product does not include a termite-proofing treatment.

2. The method of claim 1, further comprising waiting at least three months between said injecting step and said felling step.

3. The method of claim 1, wherein the insecticide is thiamethoxam.

4. The method of claim 1, wherein the at least one solvent is selected from the group consisting of lower alcohols, glycols and their derivatives, ethers, ketones, esters, sulfoxides, nitrites, pyrrolidones, glycerins and amides.

5. The method of claim 1, wherein the at least one surfactant is selected from the group consisting of polyoxyalkylene hardened caster oils, polyoxyethylene alkyl ethers, polyoxyethylene polyoxypropylene alkyl ethers, polyoxyethylene sorbitan fatty acid esters, polyoxyethylene sorbitol fatty acid esters, polyglycerin fatty acid esters, sucrose fatty acid esters, polyoxyalkylene (poly)styrene phenols, and polyoxyalkylene(poly)styrene cresols and their sulphate esters and phosphate esters and their salts.

6. The method of claim 1, wherein the neonicotinoid-based insecticide component is present from 0.1 to 20 wt %, the at least one solvent is present from 30 to 90 wt %, and the at least one surfactant is present less than 20 wt %, wherein said wt % is based on the weight of the liquid mixture.

7. The method of claim 1, wherein the neonicotinoid-based insecticide component is present from 1.0 to 10 wt %, the at least one solvent is present from 40 to 70 wt %, and the at least one surfactant is present less than 10 wt %, wherein said wt % is based on the weight of the liquid mixture.

* * * * *